US012656352B2

(12) United States Patent
Lee et al.

(10) Patent No.: US 12,656,352 B2
(45) Date of Patent: Jun. 16, 2026

(54) AMINO ACID, ORGANIC COMPOUND AND OXYLIPIDIN BIOMARKERS IN BLOOD FOR MACULAR EDEMA AND USE THEREOF

(71) Applicants: KONKUK UNIVERSITY INDUSTRIAL COOPERATION CORPORATION, Seoul (KR); UNIVERSITY-INDUSTRY COOPERATION GROUP OF KYUNG HEE UNIVERSITY, Yongin-si (KR)

(72) Inventors: Choon-Hwan Lee, Seoul (KR); Jeong-Taek Woo, Seoul (KR); Sang-Youl Rhee, Seoul (KR); Eun-Sung Jung, Suwon-si (KR)

(73) Assignees: KONKUK UNIVERSITY INDUSTRIAL COOPERATION CORPORATION, Seoul (KR); UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 861 days.

(21) Appl. No.: 17/923,478

(22) PCT Filed: May 6, 2021

(86) PCT No.: PCT/KR2021/005642
§ 371 (c)(1),
(2) Date: Nov. 4, 2022

(87) PCT Pub. No.: WO2021/225371
PCT Pub. Date: Nov. 11, 2021

(65) Prior Publication Data
US 2023/0194551 A1     Jun. 22, 2023

(30) Foreign Application Priority Data

May 6, 2020    (KR) ........................ 10-2020-0053852

(51) Int. Cl.
G01N 33/68       (2006.01)
G01N 30/72       (2006.01)
G01N 30/88       (2006.01)
(52) U.S. Cl.
CPC ......... *G01N 33/6893* (2013.01); *G01N 30/72* (2013.01); *G01N 30/88* (2013.01);
(Continued)
(58) Field of Classification Search
CPC .................................................. G01N 33/6893
(Continued)

(56) References Cited

U.S. PATENT DOCUMENTS

2013/0345175 A1*  12/2013  Beisswenger ...... G01N 33/6893
                                                        514/86
2018/0340926 A1*  11/2018  Beisswenger .......... G01N 33/50

FOREIGN PATENT DOCUMENTS

JP        2010-085363 A      4/2010
KR        10-2000827 B1      7/2019

OTHER PUBLICATIONS

Rhee, S. Y. et al, Metabolomics 2018, 14, article 89, 10 pages. (Year: 2018).*

(Continued)

*Primary Examiner* — Arlen Soderquist
(74) *Attorney, Agent, or Firm* — Sughrue Mion, PLLC

(57) ABSTRACT

In the present invention, among blood metabolites, amino acids, organic compounds and oxylipins that were statistically significantly differentiated from the control group, were selected from type 2 diabetes patients. Specifically, asparagine, aspartic acid, glutamic acid, cysteine, lysine, (Continued)

citric acid, and uric acid, and 12-oxo ETE, 15-oxo ETE, 9-oxo ODE, and 20-carboxy leukotriene B4, which are oxylipins, were confirmed to have cutoff values of AUC>0.7. In addition, the blood metabolites showed a significant difference between a DME patient group and a non-DME patient group, and thus were confirmed to be usable for accurate diagnosis of DME.

9 Claims, 7 Drawing Sheets

(52) U.S. Cl.
CPC . *G01N 33/6851* (2013.01); *G01N 2030/8818* (2013.01); *G01N 2030/884* (2013.01); *G01N 2800/042* (2013.01); *G01N 2800/16* (2013.01)

(58) Field of Classification Search
USPC .......................................................... 436/89
See application file for complete search history.

(56) References Cited

OTHER PUBLICATIONS

Zhu, X.-R. et al, Nutrition & Metabolism 2019, 16, article 37, 11 pages. (Year: 2019).*

Ibrahim, A. S. et al, Journal of Lipid Research 2015, 56, 599-611. (Year: 2015).*
Chistyakov, D. V. et al, Biomedicines 2020, 8, Article 344, 22 pages. (Year: 2020).*
Libuse Krizova el al., "Increased uric acid and glucose concentrations in vitreous and serum of patients with diabetic macular oedema", Ophthalmic Res., Jan. 14, 2011, vol. 46, No. 2 (Retrieved on Aug. 1, 2021]. Retrieved from <https://pubmed.ncbi.nhn.nih.gOv/21242702/<>DOI: 10.1159/000322994>.
Libuse Krizova et al., "Correlation of Vitreous Vascular Endothelial Growth Factor and Uric Acid Concentration Using Optical Coherence Tomography in Diabetic Macular Edema", Journal of Ophthalmology, Nov. 17, 2015, vol. 2015, Article ID 478509, 7 pages, [Retrieved on Aug. 1, 2021 ]. Retrieved from <https://pubmed.ncbi.nlm.nih.gov/26682064/<>DOI: 10.1155/2015/478509>.
S. A Shippy et al., "Elevation of Vitreous Glutamate Levels With Diabetic Macular Edema", ARVO Annual Meeting, May 31, 2008, [Retrieved on Aug. 1, 20211. Retrieved from <https://iovs.arvojournals.org/article.aspx?articleid=2375562>.
International Search Report of PCT/KR2021/005642 dated Aug. 13, 2021 [PCT/ISA/210].

* cited by examiner

AMINO ACID, ORGANIC COMPOUND AND OXYLIPIDIN BIOMARKERS IN BLOOD FOR MACULAR EDEMA AND USE THEREOF

CROSS REFERENCE TO RELATED APPLICATIONS

This application is a National Stage of International Application No. PCT/KR2021/005642, filed May 6, 2021, claiming priority to Korean Patent Application No. 10-2020-0053852, filed May 6, 2020, the entire disclosures of which are incorporated herein by reference.

TECHNICAL FIELD

The present invention relates to a biomarker in blood for diabetic macular edema and a use thereof.

BACKGROUND ART

As the duration of diabetes increases, various systemic complications are accompanied, and as typical complications of diabetes, cardiovascular disease, diabetic nephropathy, diabetic neuropathy, and diabetic macular edema occur. As the prevalence and duration of disease in diabetic patients increase, the importance of diabetic complications is also increasing. In particular, diabetic retinopathy is associated with hyperglycemia and is known as a complication that severely impairs the quality of life of diabetic patients. However, although the diagnosis and treatment of the diabetic retinopathy is a method of improving the life quality of patients, in accurate diagnosis and treatment of diabetic retinopathy, satisfactory results have never been reported compared with other complications.

The diabetic retinopathy is generally classified into mild, moderate, and severe non-proliferative and proliferative retinopathy depending on the degree of angiogenesis, but in diabetic patients, the most directly associated complication of blindness is diabetic macular edema (DME). The diabetic macular edema is known as a disease accompanied by the thickened retina and hard exudation containing the macula. It is known that such macular edema is closely associated with the exudation process of vascular endothelial cells and plasma proteins.

It is estimated that about 10% of patients with diabetic retinopathy have diabetic macular edema, and in general, as diabetic retinopathy progresses, the prevalence of diabetic macular edema also increases. However, since the diabetic macular edema is not necessarily accompanied even if the diabetic retinopathy is severe, there is a need for a biomarker capable of accurately diagnosing diabetic macular edema.

DISCLOSURE

Technical Problem

An object of the present invention is to provide a composition for diagnosing diabetic macular edema (DME) including a preparation for measuring the expression levels of one or more metabolites selected from the group consisting of plasma amino acids, organic compounds and oxylipins in a biological sample.

Another object of the present invention is to provide a kit for diagnosing diabetic macular edema (DME) including the composition.

Yet another object of the present invention is to provide a method for providing information required for diagnosis of diabetic macular edema including measuring the expression levels of one or more metabolites selected from the group consisting of plasma amino acids, organic compounds and oxylipins using the kit in a biological sample of a subject; and comparing the measured expression levels of the metabolites with the levels of metabolites of a control sample.

Yet another object of the present invention is to provide a screening method of drugs for preventing or treating diabetic macular edema including treating a tested material to a subject with diabetic macular edema; and selecting a material for reducing the expression levels of one or more metabolites selected from the group consisting of plasma amino acids, organic compounds and oxylipins compared to an untreated control group in a biological sample of a subject treated with the tested material.

Yet another object of the present invention is to provide a method for diagnosis of diabetic macular edema including measuring the expression levels of one or more metabolites selected from the group consisting of plasma amino acids, organic compounds and oxylipins using the kit in a biological sample of a subject; and comparing the measured expression levels of the metabolites with the levels of metabolites of a control sample.

Technical Solution

An aspect of the present invention provides a composition for diagnosing diabetic macular edema (DME) including a preparation for measuring the expression levels of one or more metabolites selected from the group consisting of plasma amino acids, organic compounds and oxylipins in a biological sample.

Further, another aspect of the present invention provides a kit for diagnosing diabetic macular edema (DME) including the composition.

Further, yet another aspect of the present invention provides a method for providing information required for diagnosis of diabetic macular edema including measuring the expression levels of one or more metabolites selected from the group consisting of plasma amino acids, organic compounds and oxylipins using the kit in a biological sample of a subject; and comparing the measured expression levels of the metabolites with the levels of metabolites of a control sample.

Further, yet another aspect of the present invention provides a screening method of drugs for preventing or treating diabetic macular edema including treating a tested material to a subject with diabetic macular edema; and selecting a material for reducing the expression levels of one or more metabolites selected from the group consisting of plasma amino acids, organic compounds and oxylipins compared to an untreated control group in a biological sample of a subject treated with the tested material.

Further, yet another aspect of the present invention provides a method for diagnosis of diabetic macular edema including measuring the expression levels of one or more metabolites selected from the group consisting of plasma amino acids, organic compounds and oxylipins using the kit in a biological sample of a subject; and comparing the measured expression levels of the metabolites with the levels of metabolites of a control sample.

Advantageous Effects

According to the present invention, among blood metabolites, amino acids, organic compounds and oxylipins that were statistically significantly differentiated from a control group, were selected from type 2 diabetes patients. Among them, asparagine, aspartic acid, glutamic acid, cysteine, lysine, citric acid, and uric acid, and 12-oxo ETE, 15-oxo ETE, 9-oxo ODE, and 20-carboxy leukotriene B4, which are oxylipins, can be used as biomarkers of diabetic macular edema, and were confirmed to have high sensitivity and specificity. Therefore, the biomarkers can be usefully used for diagnosis of diabetic macular edema.

BEST MODE FOR THE INVENTION

Figure 1:
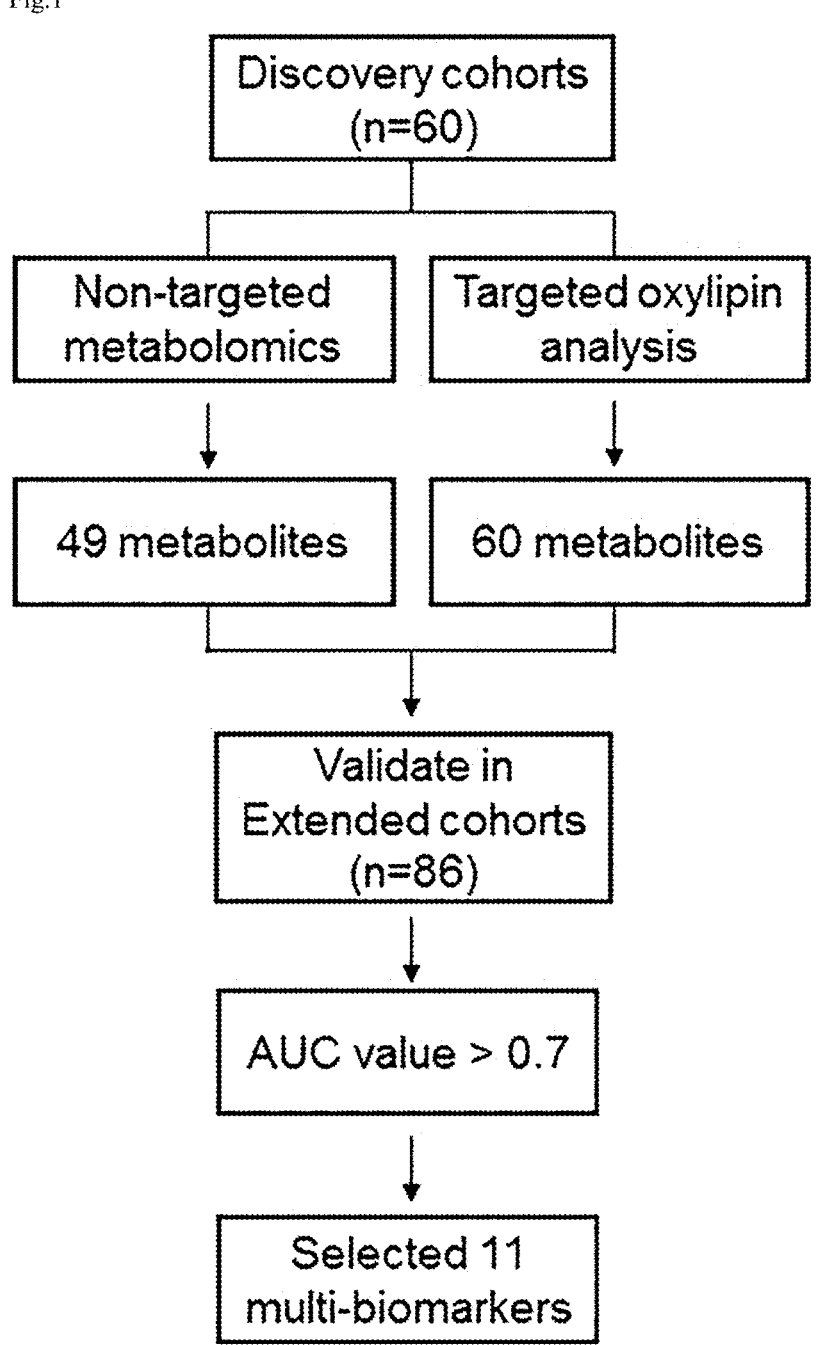
FIG. 1 is a diagram schematically illustrating a discovery process of biomarkers for the diagnosis of diabetic macular edema of the present invention.

Hereinafter, the present invention will be described in detail.

The present invention provides a composition for diagnosing diabetic macular edema (DME) including a preparation for measuring the expression levels of one or more metabolites selected from the group consisting of plasma amino acids, organic compounds and oxylipins in a biological sample.

In the present invention, the "metabolites" refer to metabolites obtained from a sample having a biological origin, and the metabolites are preferably plasma amino acids or organic compounds. In addition, the sample may be pretreated to detect the metabolites. For example, the pretreating may include filtration, distillation, extraction, concentration, inactivation of interfering components, addition of reagents, and the like. In addition, the metabolites may include materials produced by metabolisms and metabolic processes, materials generated by chemical metabolisms by biological enzymes and molecules, or the like.

In the present invention, the "preparation for measuring the expression levels" refers to a preparation for quantitatively detecting amino acids or organic compounds in blood from a biological sample isolated from a diabetic patient, and the preparation is not particularly limited, and may be a reagent or chemical material capable of quantifying the metabolites.

According to an example of the present invention, the plasma amino acids and the organic compounds may be one or more selected from the group consisting of asparagine, aspartic acid, glutamic acid, cysteine, lysine, citric acid and uric acid.

According to an example of the present invention, the oxylipins may be one or more selected from the group consisting of 12-oxo ETE, 15-oxo ETE, 9-oxo ODE and 20-carboxy leukotriene B4.

In the present invention, the "expression levels of the metabolites" refer to the concentrations of the metabolites or the amounts of the metabolites, and the levels of the metabolites may be measured by using, one or more selected from the group consisting of, for example, chromatography/mass spectrometry, light absorption spectrometry, emission spectroscopy, nuclear magnetic resonance spectroscopy, ultraviolet spectroscopy, infrared spectroscopy, fluorescence spectroscopy, enzyme-linked immunosorbent assay (ELISA) and mass spectrometry, but are not limited thereto, and all quantitative methods commonly used in the art may be used.

According to an example of the present invention, the chromatography/mass spectrometry may be characterized by liquid chromatography triple quadrupole mass spectrometry (LC-triple-Q-MS) or gas chromatography/time-offlight mass spectrometry (GC-TOF-MS).

In the metabolites of the present invention, respective ingredients are isolated by LC or GC, and constituents may be identified through structural information (elemental composition) as well as accurate molecular weight information using information obtained through triple-Q-MS or TOF-MS.

According to an example of the present invention, the biological sample may be a composition selected from the group consisting of blood, plasma, serum, urine, tears, sputum, nasal secretion, bronchial secretion, bronchial lavage fluid, pulmonary secretion, and alveolar lavage fluid.

According to an example of the present invention, the diabetes may be type 2 diabetes.

In addition, the composition may further include a detection reagent. The detection reagent may be a conjugate labeled with a detector such as a chromogenic enzyme, a fluorescent material, a radioactive isotope, or a colloid. The chromogenic enzyme may be peroxidase, alkaline phosphatase, or acid phosphatase, and the fluorescent material may be fluorescein carboxylic acid (FCA), fluorescein isothiocyanate (FITC), fluorescein thiourea (FTH), 7-acetoxy coumarin-3-yl, fluorescein-5-yl, fluorescein-6-yl, 2',7'-dichlorofluorescein-5-yl, 2',7'-dichlorofluorescein-6-yl, dihydro tetramethylrosamine-4-yl, tetramethylrhodamine-5-yl, tetramethylrhodamine yl, 4,4-difluoro-5,7-dimethyl-4-bora-3a,4a-diaza-s-indacen-3-ethyl or 4,4-difluoro-5,7-diphenyl-4-bora-3a,4a-diaza-s-indacen-3-ethyl, Cy3, Cy5, poly L-lysine-fluorescein isothiocyanate (FITC), rhodamine-B-isothiocyanate (RITC), phycoerythrin (PE) or rhodamine.

The detection reagent may further include a ligand capable of specifically binding to the detection reagent. The ligand may be a conjugate labeled with a detector such as a chromogenic enzyme, a fluorescent material, a radioactive isotope or colloid, and a ligand treated with streptavidin or avidin.

The composition of the present invention may include distilled water or a buffer to stably maintain the structure in addition to the detection reagent as described above.

In addition, the present invention provides a kit for diagnosing diabetic macular edema including the composition.

The diagnostic kit of the present invention may further include a quantitative device for measuring the concentrations of one or more blood metabolites selected from the group consisting of asparagine, aspartic acid, glutamic acid, cysteine, lysine, citric acid, and uric acid, and 12-oxo ETE, 15-oxo ETE, 9-oxo ODE, and 20-carboxy leukotriene B4, which are oxylipins.

In addition, the present invention provides a method for providing information required for diagnosis of diabetic macular edema including measuring the expression levels of one or more metabolites selected from the group consisting of plasma amino acids, organic compounds and oxylipins using the kit in a biological sample of a subject; and comparing the measured expression levels of the metabolites with the levels of metabolites of a control sample.

According to an example of the present invention, the method may be to determine to have or be at a risk of diabetic macular edema when the blood concentration of the metabolites is increased by comparing the control group and the subject.

According to an example of the present invention, in the method, the cutoff values of one or more metabolites selected from the group consisting of amino acids, organic compounds, and oxylipins in blood may be 0.7 or more.

In addition, the present invention provides a screening method of drugs for preventing or treating diabetic macular edema including treating a tested material to a subject with diabetic macular edema; and selecting a material for reducing the expression level of one or more metabolites selected from the group consisting of plasma amino acids, organic compounds and oxylipins compared to an untreated control group in a biological sample of a subject treated with the tested material.

In the method of the present invention, the tested material is preferably any one selected from the group consisting of peptides, proteins, non-peptide compounds, active compounds, fermentation products, cell extracts, plant extracts, animal tissue extracts, and plasma, but the present invention is not limited thereto.

In addition, the present invention provides a method for diagnosis of diabetic macular edema including measuring the expression levels of one or more metabolites selected from the group consisting of plasma amino acids, organic compounds and oxylipins using the kit in a biological sample of a subject; and comparing the measured expression levels of the metabolites with the levels of metabolites of a control sample.

MODES OF THE INVENTION

Hereinafter, the present invention will be described in more detail by Example. These Examples are to explain the present invention in more detail, and it will be apparent to those skilled in the art that the scope of the present invention is not limited to these Examples.

<Example 1> Subjects and Clinical Trial Design

A clinical trial was conducted as part of the National Biobank project, using basic characteristics of prospective cohort study registrants collected from September 2014 to July, 2015. Subjects in the cohorts were patients suffering from type 2 diabetes for at least 15 years.

The clinical information of the subjects was registered based on a multi-center clinical data registration standardization method approved by the Korean Diabetes Association, and biospecimens were collected according to the guidelines of the National Biobank of Korea.

In addition, the clinical information of the subjects was approved by the institutional review board of Kyunghee University Hospital for clinical trials (IRB No. KMC IRB 1428-04). Written consent was obtained from all subjects. In addition, clinical trial information was provided by the Clinical Research Information Service (http://cris.nih-.go.kr), a Korean national service linked with the International Clinical Trials Registry Platform (ICTRP) of the World Health Organization (CRIS, No. KCT0001269).

<Example 2> Phenotype Analysis of Diabetic
Macular Edema (DME)

The diabetic macular edema (DME) symptoms of each subject of <Example 1> were evaluated through fundus photography (FF 540 Plus; Carl Zeiss Meditech, Jena, Germany) and optical coherence tomography (HD-OCT; Carl Zeiss Meditech, Dublin, CA, USA). According to the Early Treatment Diabetic Retinopathy Study (ETDRS) criteria, the DME was classified into three categories: 1) a category with a thickness of 500 nm or more from the macular center, 2) a category with a thickness of 500 nm or more of the hard exudate and the adjacent retina from the macular center, or 3) a category in which the thickened retina was located less than 1 disk in diameter from the macular center. Two or more ophthalmologists classified a DME state based on a test result. In case of discrepancy between doctors, images were reviewed again to reach a final interpretation.

<Example 3> Statistical Analysis of Clinical Trial
Results

The clinical characteristics of DME patients and non-DME patients were compared with each other by focusing on identifying the characteristics of subjects with long-term type 2 diabetes and without retinopathy. Validation and statistical analysis of clinical data were performed independently by statisticians. Means, proportions, and distributions were compared regardless of DME in patients. After the initial analysis, case and control sets were selected through propensity score matching (PSM) with clinical characteristics similar to DME, and the same samples were used for metabolomics studies. SAS software (version 9.3, SAS Institute Inc., Cary, NC, USA) was used for all statistical analyses.

<Example 4> Metabolomics Study Using Serum
Samples

<4-1> Sample Preparation

Metabolites were extracted from 200 μl of plasma. 1 ml of methanol containing an internal standard solution (1 mg/ml of 2-chlorophenylalanine in water) was mixed with the plasma and then homogenized with a sonicator for 10 minutes. After homogenization, a suspension was maintained at 4° C. for 60 minutes and then centrifuged at 13,000 rpm and 4° C. for 10 minutes. A supernatant was filtered through a 0.2-μm polytetrafluoroethylene (PTFE) filter and dried using a high-speed vacuum concentrator (Modulspin 31; Biotron, South Korea). The dried extract was subjected to GC-TOF-MS analysis.

<4-2> GC-TOF-MS Analysis

For GC-TOF-MS analysis, the dried sample in <Example 4-1> was oximated at 30° C. for 90 minutes using 50 µl of methoxyamine hydrochloride (20 mg/ml in pyrimidine) and silylated at 37° C. for 30 minutes using 50 µl of Nmethyl-N-(trimethylsilyl) trifluoroacetamide (MSTFA). GC-TOF-MS analysis was performed using an Agilent 7890 gas chromatography system (Agilent Technologies, Palo Alto, CA, USA) coupled with an Agilent 7693 auto-sampler (Agilent Technologies) and equipped with a PegasusTI HT TOF MS system (LECO Corp., St. Joseph, MI, USA). As a column, an Rtx-5MS column (i.d., 30 m×0.25 mm, 0.25 µm particle size; Restek Corp., Bellefonte, PA, USA) was used, and helium at a flow rate of 1.5 ml/min was used as carrier gas. The sample dispensed in 1 µl was injected into the GC in a splitless mode. The temperature was maintained at 75° C. for 2 minutes, increased by 15° C./min to reach 300° C., and then maintained for 3 minutes. Front inlet and transfer line temperatures were set to 250° C. and 240° C., respectively. Electron ionization was performed at –70 eV, and full scanning was performed in the range of 50 to 1000 m/z for data collection.

<4-3> LC-Triple-Q-MS Analysis

An Oasis-HLC cartridge was used to detect oxylipins from the plasma. Before detection of oxylipins, the cartridge was washed with 2 ml of ethyl acetate, a mixed solvent (2 ml) of methanol (2×2 ml) and water, and methanol containing 0.1% acetic acid (95:5 v/v). After the cartridge was washed, 200 µl of the plasma was loaded into the cartridge. After loading the plasma, the cartridge was washed with 1.5 ml of a mixed solvent (water:methanol, 95:5 v/v, 0.1% acetic acid) under a high vacuum. The washed cartridge was dried under low vacuum conditions for 20 minutes. To elute oxylipins transferred to the dried cartridge, 0.5 ml of methanol and 2 ml of ethyl acetate were added, and 30% glycerol-containing methanol was eluted into a tube containing 6 µl of methanol. After elution, the eluate was dried using a vacuum concentrator, and after drying, the eluate was resuspended in methanol (10 mg/ml). The resuspended suspension was subjected to LC-triple-Q-MS analysis after filtration.

LC-triple-Q-MS analysis was performed with Nexera2 LC coupled with an electrospray source and triple quadruple MS. 1 µl of the resuspended suspension (5%) was injected to a Kinetex C18 column (100×2.1 mm, 2.6 µm, Phenomenex, Torrance, CA, USA) using 0.1% formic acid (solvent A) and acetonitrile (solvent B) containing 0.1% formic acid as a mobile phase. The solvent B was injected at a flow rate of 300 µL/min with a gradient of the solvent at a rate of 5% during the first 1 min, injected in a linear increase from 5% to 100% over 9 minutes, and after injection by increasing the solvent B, the solvent gradient was adjusted to decrease to 5% again for 1 minute. Additional conditions were analyzed under conditions of capillary voltage of –3000 V, capillary temperature of 450° C., vaporizer temperature of 400° C., sheath gas of 3 L/min, ion sweep gas of 2.0 Arb, auxiliary gas of 10 Arb, and dry gas of 8 L/min.

<4-4> Data Processing and Multivariate Statistical Analysis for Metabolomics Study After performing GC-TOF-MS analysis by the method described in Example <4-2>, GC-TOF-MS data was obtained and pre-processed using LECO Chroma TOF TM software (version 4.44, LECO Corp.) and converted to NetCDF format (*.cdf). In addition, after LC-triple-Q-MS analysis was performed by the method described in Example <4-3>, raw data were obtained using MassLynx software (version 4.1, Waters Corp.). The raw data file was converted to NetCDF format (*.cdf) using MassLynx DataBridge software (version 4.1, Waters Corp.). After conversion, peak detection, retention time correction, and alignment were performed using a Metalign software package (http://www.metalign.nl). The result data was stored as a Microsoft Excel file. Multivariate statistical analysis was performed using SIMCA-P+ (version 12.0; Umetrics, Umea, Sweden). Data sets were automatically scaled to have unit variance and mean-centered based on a column. Orthogonal partial least squares-discriminant analysis (OPLS-DA) was performed to compare each data set. Variables were selected based on variable importance to projection (VIP) values of OPLS-DA. Statistically significant differences were verified by ANOVA analysis, Student's t-test, and Duncan's multiple range tests using PASW Statistics 18 software (SPSS Inc., Chicago, IL, USA). Receiver operating characteristic (ROC), and curve and logistic regression analysis were obtained using Medcalc software (version 14.8.1; Medcalc Software, Mariakerke, Belgium).

<Experimental Example 1> Confirmation of Clinical Characteristics of Subjects According to PSM Clinical data and samples were collected from 198 subjects who had the consent among 220 subjects recruited by the method described in <Example 1>. After the consent, 15 subjects withdrew the consent, and ophthalmic examinations were performed on a total of 183 subjects (FIG. 1). The average age of clinical trial participants was 66.8 years, the average duration of diabetes was 22.6 years, and 50.3% of the subjects were women. Among a total of 183 clinical trial participants who took the ophthalmic examination, 124 (67.8%) were diagnosed with diabetic retinopathy (DR), and 46 (25.1%) were diagnosed with DME. Therefore, based on the results of performing PSM, as shown in Tables 1-1 to 1-6 below, 30 pairs of patients and a control group without significant difference in clinical characteristics except for the presence or absence of DME were selected, and metabolomics studies were performed on the patients. In addition, validation of results derived from the discovery sets was performed using 42 pairs of validation sets.

TABLE 1-1

| Category | Variables | Discovery cohort (30 pairs) | | | Extended cohort (43 pairs) | | |
|---|---|---|---|---|---|---|---|
| | | No ME | ME | p | No ME | ME | p |
| Clinical | Gender (female, pair) | 9 | 2 | 1 | 16 | 10 | 1 |
| characteristics | DM duration (yr) | 22.10 ± 6.78 | 23.70 ± 6.95 | 0.329 | 21.84 ± 7.27 | 23.81 ± 6.37 | 0.088 |
| | Age (yr) | 66.07 ± 8.71 | 61.73 ± 10.51 | 0.068 | 65.02 ± 8.81 | 62.33 ± 10.18 | 0.143 |
| | Height (cm) | 159 ± 9.21 | 158.73 ± 8.2 | 0.913 | 159.57 ± 9.21 | 158.63 ± 8.51 | 0.731 |
| | Weight (kg) | 61.87 ± 8.8 | 61.91 ± 8.77 | 0.988 | 62.42 ± 9.06 | 61.17 ± 8.84 | 0.456 |

TABLE 1-1-continued

| Category | Variables | Discovery cohort (30 pairs) | | | Extended cohort (43 pairs) | | |
|---|---|---|---|---|---|---|---|
| | | No ME | ME | p | No ME | ME | p |
| | BMI (kg/m$^2$) | 24.48 ± 2.96 | 24.65 ± 3.7 | 0.834 | 24.49 ± 2.83 | 24.37 ± 3.61 | 0.92 |
| | Waist circumference (cm) | 89.04 ± 7.79 | 89.58 ± 11.84 | 0.819 | 88.58 ± 7.41 | 88.27 ± 10.91 | 0.781 |
| | Systolic blood pressure (mmHg) | 123.17 ± 14.05 | 123.6 ± 14.13 | 0.897 | 125.44 ± 13.85 | 124.39 ± 14.41 | 0.515 |
| | Diastolic blood pressure (mmHg) | 69.37 ± 8.04 | 68.43 ± 10.23 | 0.635 | 70.49 ± 8.15 | 68.21 ± 9.89 | 0.235 |
| | HbA1c (%) | 8.37 ± 1.92 | 8.35 ± 1.56 | 0.974 | 8.20 ± 1.76 | 8.42 ± 1.45 | 0.586 |
| | Fasting plasma glucose (mg/dL) | 166.7 ± 71.48 | 159.93 ± 68.98 | 0.708 | 169.51 ± 81.48 | 166.67 ± 67.11 | 0.976 |

TABLE 1-2

| Category | Variables | Discovery cohort (30 pairs) | | | Extended cohort (43 pairs) | | |
|---|---|---|---|---|---|---|---|
| | | No ME | ME | p | No ME | ME | p |
| Clinical characteristics | Total cholesterol (mg/dL) | 178.1 ± 41.35 | 165.5 ± 33.46 | 0.265 | 177.58 ± 38.1 | 163.65 ± 31.72 | 0.169 |
| | Triglyceride (mg/dL) | 147.33 ± 111.43 | 154.2 ± 85.01 | 0.782 | 139.49 ± 105.01 | 143.79 ± 79.15 | 0.465 |
| | LDL cholesterol (mg/dL) | 107.8 ± 33.45 | 96.23 ± 28.89 | 0.237 | 105.3 ± 31.65 | 94.44 ± 27.8 | 0.22 |
| | HDL cholesterol (mg/dL) | 52.13 ± 19.49 | 48.63 ± 10.9 | 0.377 | 53.6 ± 18.12 | 49.86 ± 14.87 | 0.48 |
| | BUN (mg/dL) | 21.93 ± 10.5 | 19.33 ± 6.81 | 0.213 | 22.95 ± 15.43 | 21.44 ± 10.77 | 0.596 |
| | Creatinine (mg/dL) | 0.89 ± 0.43 | 0.88 ± 0.37 | 0.969 | 1.12 ± 1.29 | 1.03 ± 0.72 | 0.735 |
| | Creatinine Clearance (mL/min/1.73 m$^2$) | 91.86 ± 38.5 | 90.16 ± 33.6 | 0.828 | 89.08 ± 37.99 | 84.85 ± 34.91 | 0.664 |
| | AST (IU/L) | 23.7 ± 5.09 | 21.83 ± 6.81 | 0.194 | 22.84 ± 5.08 | 21.6 ± 6.19 | 0.206 |
| | ALT (IU/L) | 16.43 ± 3.47 | 16.1 ± 5.31 | 0.796 | 17.14 ± 5.1 | 15.51 ± 5.41 | 0.157 |
| | GGT (IU/L) | 23.03 ± 12 | 23 ± 8.55 | 0.987 | 29 ± 23.96 | 21.12 ± 8.37 | 0.094 |
| | ALP (IU/L) | 80.87 ± 27.6 | 86.63 ± 22.98 | 0.362 | 83.95 ± 28.73 | 85.47 ± 22.27 | 0.532 |

TABLE 1-3

| Category | Variables | Discovery cohort (30 pairs) | | | Extended cohort (43 pairs) | | |
|---|---|---|---|---|---|---|---|
| | | No ME | ME | p | No ME | ME | p |
| History of macrovascular complication | Hypertension (pair) | 5 | 20 | 1 | 7 | 29 | 1 |
| | Dyslipidemia (pair) | 11 | 10 | 0.48 | 14 | 14 | 1 |
| | Myocardial infarction (pair) | 0 | 0 | — | 0 | 0 | — |
| | Angina (pair) | 3 | 0 | — | 4 | 0 | — |
| | Heart failure (pair) | 0 | 0 | — | 1 | 0 | — |
| | Atrial fibrillation (pair) | 0 | 0 | — | 2 | 0 | — |
| | Any stroke (pair) | 2 | 1 | 0.683 | 3 | 1 | 1 |

TABLE 1-4

| Category | Variables | Discovery cohort (30 pairs) | | | Extended cohort (43 pairs) | | |
|---|---|---|---|---|---|---|---|
| | | No ME | ME | p | No ME | ME | p |
| History of microvascular complication | Retinopathy (pair) | 2 | 14 | 0.01 | 3 | 21 | 0.002 |
| | Glaucoma (pair) | 3 | 1 | 1 | 3 | 1 | 0.228 |
| | Cataract (pair) | 6 | 11 | 1 | 9 | 15 | 1 |
| | Chronic Kidney Disease (pair) | 5 | 1 | 1 | 7 | 3 | 1 |
| | Peripheral neuropathy (pair) | 8 | 7 | 0.814 | 11 | 12 | 0.556 |
| | Autonomic neuropathy (pair) | 6 | 5 | 1 | 6 | 6 | 0.789 |

TABLE 1-5

| | | Discovery cohort (30 pairs) | | | Extended cohort (43 pairs) | | |
|---|---|---|---|---|---|---|---|
| Category | Variables | No ME | ME | p | No ME | ME | p |
| Current | Metformin (pair) | 4 | 18 | 1 | 7 | 20 | 0.803 |
| Medications | Sulfonylurea (pair) | 7 | 11 | 0.773 | 13 | 12 | 0.383 |
| | DPP-4 inhibitor (pair) | 8 | 2 | 0.579 | 10 | 3 | 0.628 |
| | Meglitinide (pair) | 1 | 0 | 1 | 2 | 0 | 0.683 |
| | Thiazolidine dione (pair) | 1 | 0 | 1 | 2 | 0 | 1 |
| | SGLT-2 inhibitor (pair) | 0 | 0 | — | 0 | 0 | — |
| | Alpha glucosidase inhibitor (pair) | 0 | 0 | — | 0 | 0 | — |
| | Rapid acting insulin (pair) | 5 | 3 | 1 | 8 | 4 | 1 |
| | Basal insulin (pair) | 9 | 5 | 1 | 13 | 8 | 0.677 |
| | Pre-mixed insulin (pair) | 3 | 2 | 1 | 4 | 2 | 0.547 |

15

TABLE 1-6

| | | Discovery cohort (30 pairs) | | | Extended cohort (43 pairs) | | |
|---|---|---|---|---|---|---|---|
| Category | Variables | No ME | ME | p | No ME | ME | P |
| Current | GLP-1 agonist (pair) | 0 | 0 | — | 0 | 0 | — |
| Medications | Angiotensin Receptor Blocker (pair) | 8 | 9 | 0.789 | 11 | 12 | 0.48 |
| | Angiotensin Converting Enzyme inhibitor (pair) | 0 | 0 | 0.074 | 2 | 0 | 0.289 |
| | Calcium channel blocker (pair) | 6 | 2 | 1 | 9 | 3 | 0.823 |
| | Diuretics (pair) | 5 | 1 | 0.221 | 6 | 1 | 0.505 |
| | Beta blocker (pair) | 4 | 1 | 0.683 | 6 | 3 | 0.289 |
| | Statin (pair) | 10 | 8 | 1 | 12 | 12 | 1 |
| | Fibrate (pair) | 1 | 0 | 1 | 1 | 0 | — |
| | Aspirin (pair) | 5 | 1 | 1 | 8 | 2 | 0.387 |
| | Clopidogrel (pair) | 4 | 0 | 0.683 | 6 | 0 | 0.752 |
| | Cilostazol (pair) | 8 | 4 | 0.387 | 11 | 9 | 0.211 |

*expressed as mean ± SD, or n (%). by Paired sample t-test, or McNemar's test.

*ME, macular edema; DM, diabetes mellitus; BMI, body mass index; LDL, Low density lipoprotein; HDL, high density lipoprotein; BUN, blood urea nitrogen; AST, aspartate aminotransferase; ALT, alanine aminotransferase; GGT, gamma-glutamyl transferase; ALP, alkaline phosphatase; CAG, coronary angiography; DPP, dipeptidylpeptidase; SGLT, sodium-glucose transporter.

<Experimental Example 2> Discovery of Multi-Biomarkers of DME in Plasma

Based on the metabolomics study, multi-biomarkers in the plasma that were helpful in diagnosing DME among non-DME subjects were examined (FIG. 1). Metabolites that discriminated metabolomes with or without DME were identified and selected as candidate metabolite biomarkers. The candidate metabolite biomarkers were identified in extended cohorts by comparing relative levels. Multi-bio-markers to differentiate between DME and non-DME sub-jects were finally selected for the following qualifications: 1) Statistically significant differential metabolites and 2) metabolites satisfying conditions showing excellent dis-crimination against DME to non-DME subjects with the area under the curve (AUC)>0.7 were selected from the discov-ered and extended cohort.

Figure 2A:
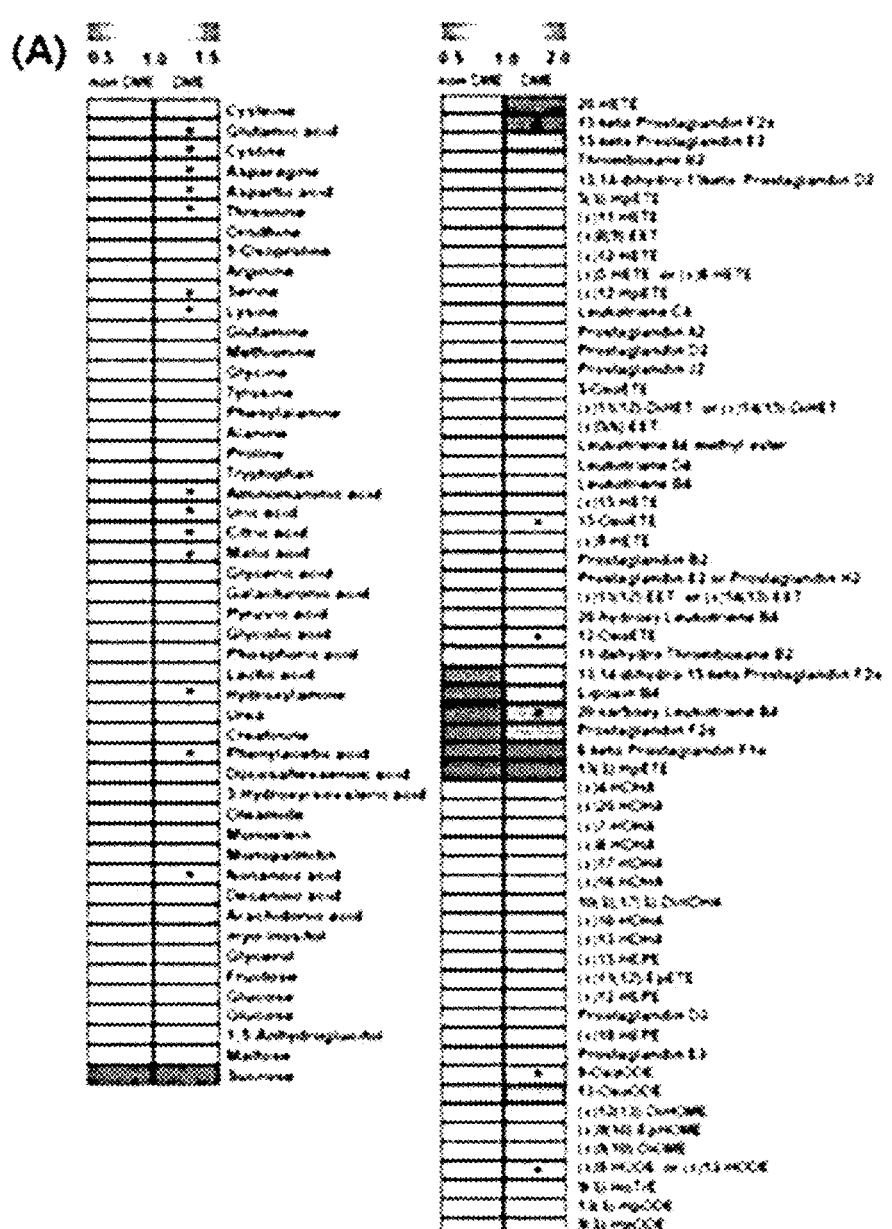
FIG. 2A illustrates a heat map normalized as average values of relative metabolite levels in DME and non-DME patient groups of the present invention.
Figure 2B:
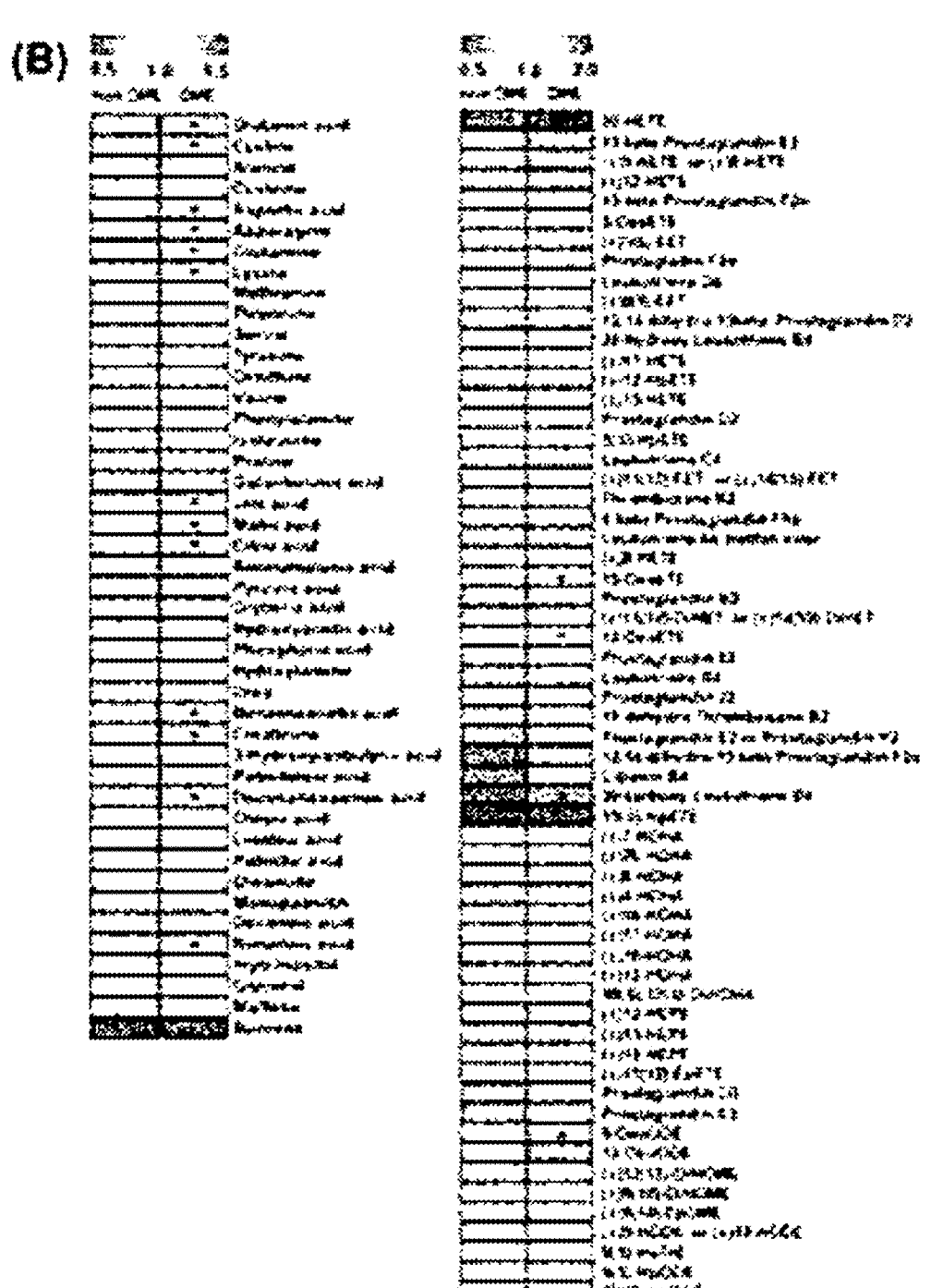
FIG. 2B illustrates a heat map normalized as average values of relative metabolite levels in DME and non-DME patient groups of the present invention.

<Experimental Example 2-1> Analysis of Metabolites and Oxylipins in Plasma Based on GC-TOF-MS Analysis Metabolite profiling based on GC-TOF-MS analysis was performed using the plasma in the discovery cohorts with multivariate statistical analysis. In a PLS-DA model, DME and non-DME groups clearly showed a difference in PLS1 (8.2%). The quality of the PLS-DA model was confirmed by $R^2Y$(cum)=0.847, $Q^2$(cum)=0.546, and cross-validation analysis (7.77e-7), indicating a valid model, and confirmed to indicate a difference between the DME group and the non-DME group. It was confirmed that the separated, VIP value of PLS-DA>0.7 was applied. A total of 49 metabolites, including 19 amino acids, 14 organic compounds, 8 fatty acids and lipids, and 8 carbohydrates, were identified as metabolites that had a difference between groups of subjects with DME and non-DME, and a total of 60 oxylipins were identified by targeted analysis. The oxylipins included 36 arachidone-derived, 9 DHA-derived, 6 EPA-derived and 9 linoleic acid-derived oxylipins, and the relative metabolite levels were normalized to mean values and visualized as heat maps (FIGS. 2A and 2B).

Figure 3A:
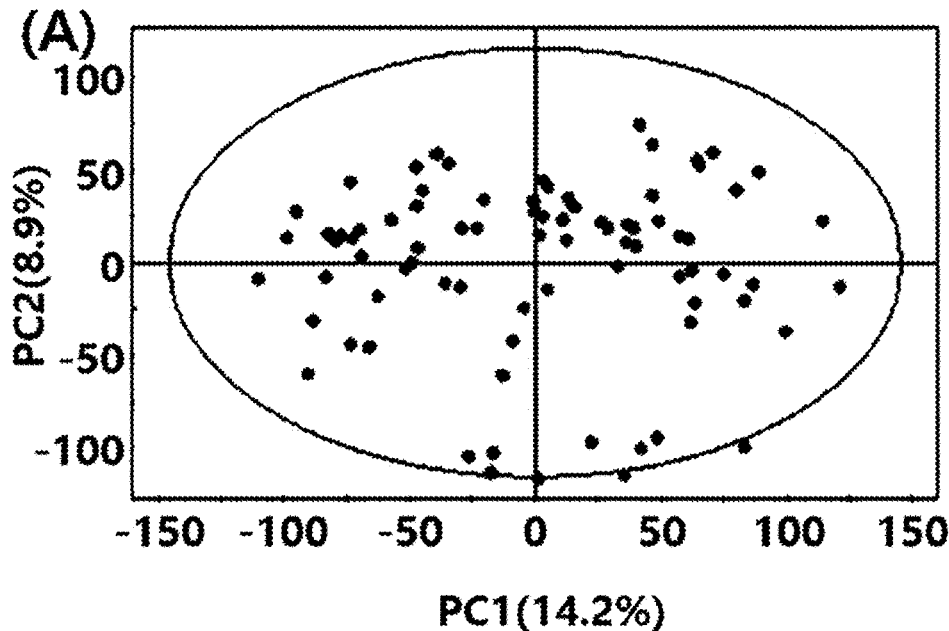
FIG. 3A is a diagram illustrating plasma main component analysis results for DME and non-DME patient groups analyzed by GC-TOF-MS of the present invention (red plots: DME group, black plots: non-DME group).
Figure 3B:
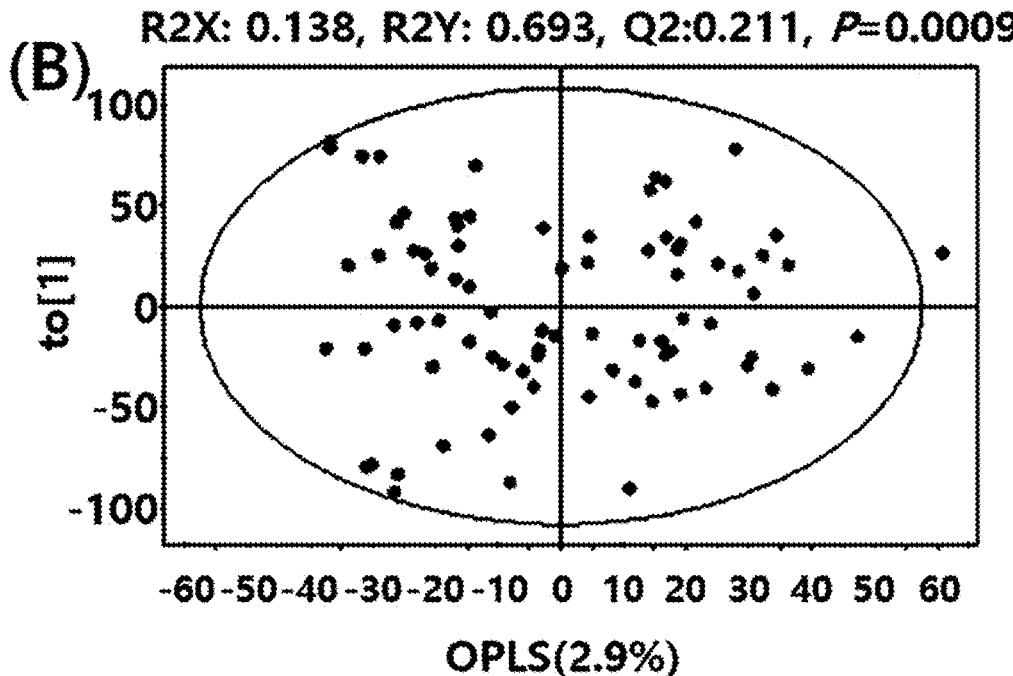
FIG. 3B is a diagram illustrating OPLS-DA score plots for DME and non-DME patient groups analyzed by GC-TOF-MS of the present invention (red plots: DME group, black plots: non-DME group).
Figure 4A:
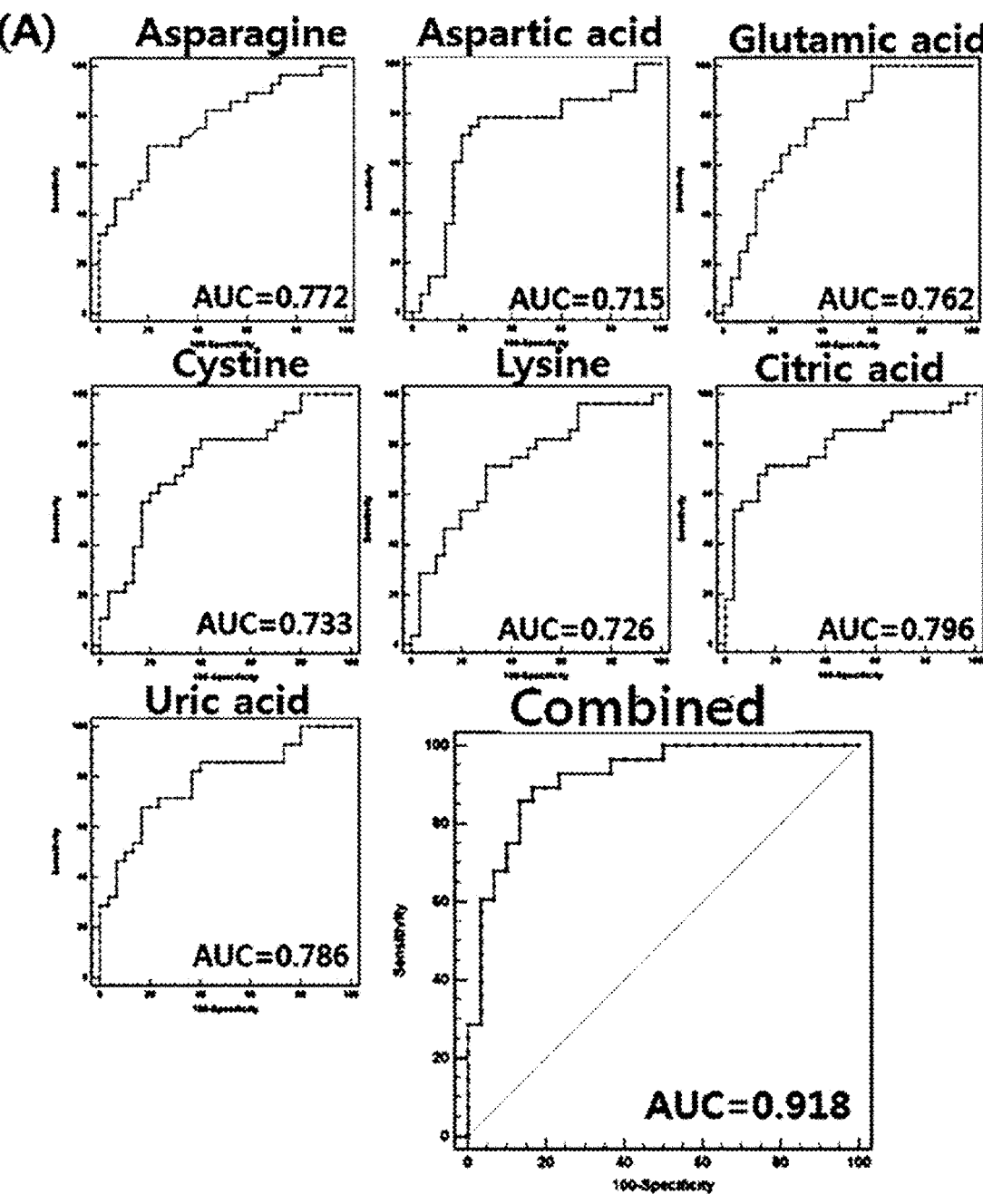
FIG. 4A is a diagram illustrating AUC values of selected biomarkers having cutoff values (AUC)>0.7 or higher and a combination thereof as compared to DME and non-DME patient groups of the present invention (asparagine, aspartic acid, glutamic acid, cysteine, lysine, citric acid, uric acid and a combination).
Figure 4B:
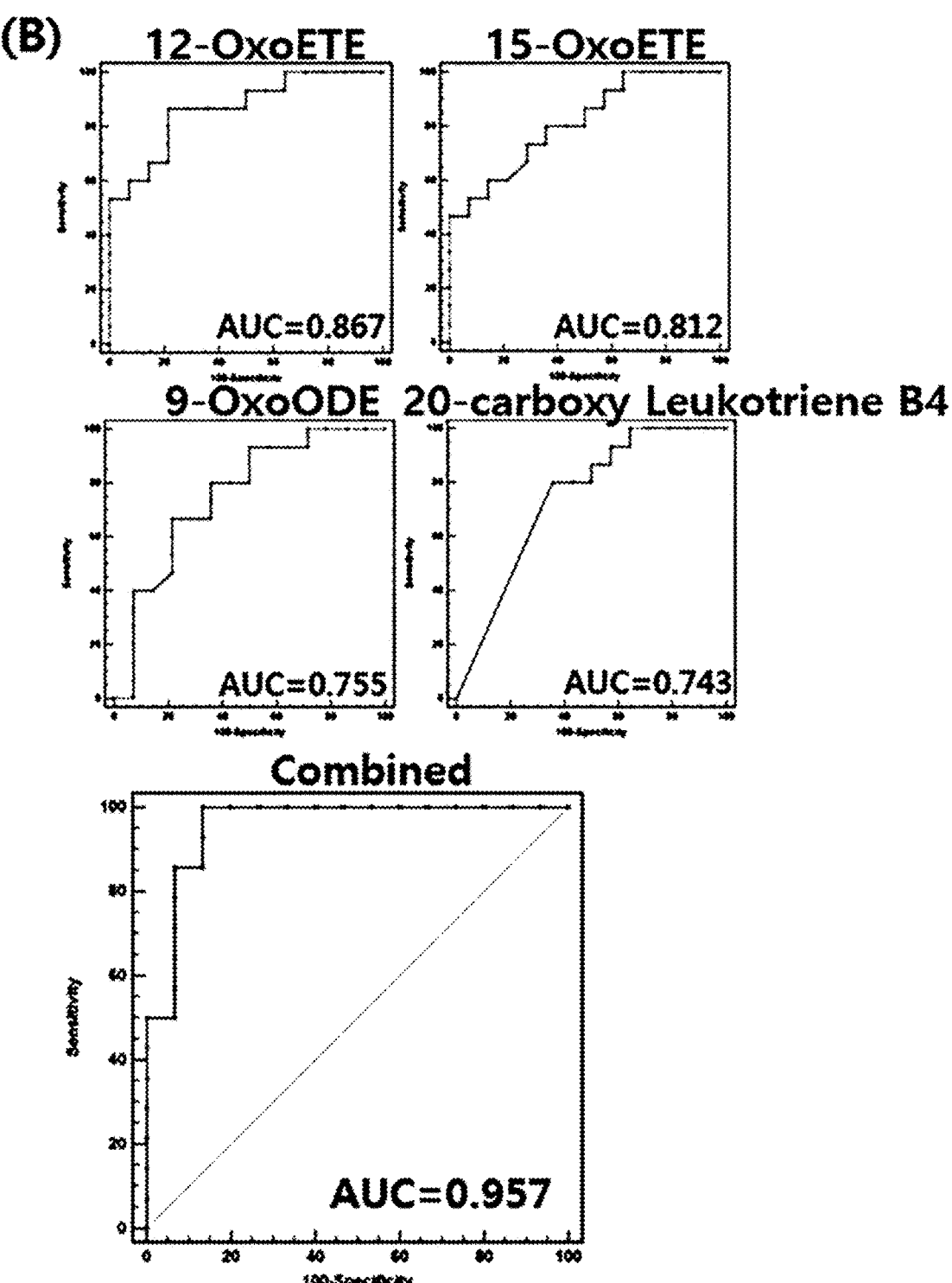
FIG. 4B is a diagram illustrating AUC values of selected biomarkers having cutoff values (AUC)>0.7 or higher and a combination thereof as compared to DME and non-DME patient groups of the present invention (12-oxo ETE, 15-oxo ETE, 9-oxo ETE, 20-carboxy leukotriene B4, and a combination).

<Experimental Example 2-2> Verification of Plasma Metabolite Biomarkers for DME Distinguished from Non-DME To determine whether plasma metabolites derived from the discovery cohorts may be used as biomarkers, in the group of <Experimental Example 1>, the present inventors further performed multivariate analysis and oxylipins pro-filing using the extended cohorts. PCA and OPLS-DA score plots showed similar trends to the discovery cohorts (FIGS. 3A and 3B). However, the OPLS-DA model values were $R^2Y$(cum)=0.693 and $Q^2$(cum)=0.211, and the fitness and predictive accuracy of the model were lower than those of the discovery cohorts, but the quality of the model was evaluated by cross-validation analysis, and the metabolites discriminated between non-DME and DME selected accord-ing to the VIP values (>0.7) of the extended cohorts, and the relative contents were visualized as heat maps. Comparison of heat maps induced from relative metabolite levels between the discovery cohorts and the extended cohorts, and the DME and non-DME patient groups was confirmed to have similar trends. Multi-biomarkers for diagnosing DME patients were finally selected and met all of the following qualifications. 1) statistically significant discriminant metabolites from both discovery cohorts and extended cohorts, and 2) metabolites with good discrimination against DME to non-DME subjects with area under the curve (AUC)>0.7. Among metabolites that satisfy all of the conditions, glutamic acid, cysteine, asparagine, aspartic acid, lysine, uric acid, malic acid, citric acid, nonanoic acid, 15-oxo ETE, 12-oxo ETE, 20-carboxy leukotriene B4 and 9-oxo ODE were statistically significant. There were also different levels between groups of subjects with DME and non-DME in both the discovery cohorts and extended cohorts. In addition, ROC curves were constructed for 109 assigned blood metabolites (Tables 2-1 to 3-4) using the relative metabolite contents of the discovery cohorts of the experimental group. Among them, the metabolites showed excellent differences for diabetes to DME with area under the curve (AUC)>0.7, and included glutamic acid (0.762), cysteine (0.733), asparagine (0.772), aspartic acid (0.715), and lysine (0.726), and were confirmed to have uric acid (0.786), citric acid (0.796), phenylacetic acid (0.810), 15-ketoprostaglandin F2α (0.750), 15-ketoprostaglandin E2 (0.719), 15-oxo ETE (0.812), 12-oxo ETE (0.867), 20-carboxy leukotriene B4 (0.743), 9-oxo ODE (0.755) and (+) 9-HODE or 13-HODE (0.743) (FIGS. 4A and 4B). Finally, the multi-biomarkers selected to diagnose DME patients from non-DME subjects were asparagine (0.729 fold), and confirmed to have aspartic acid (0.782 fold), glutamic acid (0.653 fold), cysteine (0.666 fold), lysine (0.849 fold), citric acid (0.741 fold), uric acid (0.707 fold), 12-oxo ETE (1.526 fold), 15-oxo ETE (1.319 fold), 9-oxo ODE (0.692 fold) and 20-carboxyleukotriene B4 (5.575 fold). Based on GC-TOF-MS analysis, as a result of combining the metabolites for the diagnosis of DME, the metabolite profiling, including asparagine, aspartic acid, and glutamic acid, had highly improved specificity to discriminate the DME subject group and the non-DME subjects when being combined with cysteine, lysine, citric acid and uric acid, and the combined AUC value was 0.918 (FIG. 4A). In addition, the combination of oxylipins including 12-oxo ETE, 15-oxo ETE, 9-oxo ODE and 20-carboxy leukotriene B4 calculated a combined AUC value of 0.957 (FIG. 4B), and had an excellent ability of discriminating the DME subjects from the non-DME subjects. Finally, asparagine, aspartic acid, glutamic acid, cysteine and lysine derived from plasma amino acids, citric acid and uric acid derived from organic compounds, and 12-oxo ETE, 15-oxo ETE, 9-oxo ODE and 20-carboxyleukotriene B4 as oxylipins were selected and used as biomarkers to distinguish DME and non-DME.

TABLE 2-1

| No. | RT (min) | Unique Mass | Metabolites | AUC | Fold Change (DME/DB) | t-test |
|---|---|---|---|---|---|---|
| 1 | 9.75 | 220 | Cysteine | 0.658 | 0.645 | 0.0934 |
| 2 | 10.23 | 246 | Glutamic acid | 0.762 | 0.653 | 0.0003 |
| 3 | 14.76 | 218 | Cystine | 0.733 | 0.666 | 0.0015 |
| 4 | 10.66 | 116 | Asparagine | 0.772 | 0.729 | 0.0006 |
| 5 | 9.45 | 232 | Aspartic acid | 0.715 | 0.782 | 0.013 |
| 6 | 8.31 | 219 | Threonine | 0.67 | 0.819 | 0.0296 |
| 7 | 11.72 | 142 | Ornithine | 0.682 | 0.82 | 0.0504 |
| 8 | 9.51 | 156 | 5-Oxoproline | 0.676 | 0.826 | 0.1042 |
| 9 | 10.19 | 142 | Arginine | 0.62 | 0.842 | 0.2285 |
| 10 | 8.06 | 204 | Serine | 0.692 | 0.843 | 0.0463 |
| 11 | 12.45 | 174 | Lysine | 0.726 | 0.849 | 0.0041 |
| 12 | 11.12 | 156 | Glutamine | 0.621 | 0.857 | 0.0867 |

TABLE 2-1-continued

| No. | RT (min) | Unique Mass | Metabolites | AUC | Fold Change (DME/DB) | t-test |
|---|---|---|---|---|---|---|
| 13 | 9.45 | 176 | Methionine | 0.602 | 0.878 | 0.0985 |
| 14 | 7.58 | 174 | Glycine | 0.664 | 0.88 | 0.0837 |
| 15 | 12.58 | 218 | Tyrosine | 0.536 | 0.941 | 0.409 |
| 16 | 10.33 | 218 | Phenylalanine | 0.576 | 0.95 | 0.3471 |
| 17 | 5.56 | 116 | Alanine | 0.542 | 1.08 | 0.4789 |

TABLE 2-2

| No. | RT (min) | Unique Mass | Metabolites | AUC | Fold Change (DME/DB) | t-test |
|---|---|---|---|---|---|---|
| 18 | 7.5 | 142 | Proline | 0.524 | 1.098 | 0.3269 |
| 19 | 14.46 | 204 | Tryptophan | 0.562 | 1.245 | 0.2263 |
| 20 | 9.04 | 218 | Aminomalonic acid | 0.693 | 0.693 | 0.0051 |
| 21 | 13.64 | 441 | Uric acid | 0.786 | 0.707 | 0.0001 |
| 22 | 11.76 | 273 | Citric acid | 0.796 | 0.741 | 0.0001 |
| 23 | 9.18 | 233 | Malic acid | 0.688 | 0.749 | 0.0169 |
| 24 | 7.8 | 189 | Glyceric acid | 0.638 | 0.803 | 0.0735 |
| 25 | 12.64 | 333 | Galacturonic acid | 0.62 | 0.859 | 0.3721 |
| 26 | 5.05 | 174 | Pyruvic acid | 0.566 | 0.894 | 0.343 |

TABLE 2-3

| No. | RT (min) | Unique Mass | Metabolites | AUC | Fold Change (DME/DB) | t-test |
|---|---|---|---|---|---|---|
| 27 | 5.29 | 177 | Glycolic acid | 0.59 | 0.914 | 0.2367 |
| 28 | 7.32 | 299 | Phosphoric acid | 0.519 | 1.049 | 0.4954 |
| 29 | 5.15 | 117 | Lactic acid | 0.562 | 1.059 | 0.2686 |
| 30 | 5.7 | 133 | Hydroxylamine | 0.64 | 1.155 | 0.0318 |
| 31 | 7.06 | 189 | Urea | 0.63 | 1.223 | 0.0749 |
| 32 | 9.79 | 115 | Creatinine | 0.652 | 1.239 | 0.0946 |
| 33 | 7.51 | 164 | Phenylacetic acid | 0.81 | 1.393 | 0 |
| 34 | 16.12 | 91 | Docosahexaenoic acid | 0.6 | 0.805 | 0.0797 |
| 35 | 6.61 | 131 | 3-Hydroxy-isovaleric acid | 0.528 | 0.929 | 0.3489 |
| 36 | 15.35 | 131 | Oleamide | 0.56 | 1.037 | 0.4464 |
| 37 | 17.07 | 397 | Monoolein | 0.518 | 1.039 | 0.7291 |
| 38 | 16.23 | 371 | Monopalmitin | 0.602 | 1.135 | 0.1011 |
| 39 | 8.01 | 215 | Nonanoic acid | 0.671 | 1.171 | 0.0332 |

TABLE 2-4

| No. | RT (min) | Unique Mass | Metabolites | AUC | Fold Change (DME/DB) | t-test |
|---|---|---|---|---|---|---|
| 40 | 8.86 | 229 | Decanoic acid | 0.691 | 1.192 | 0.0881 |
| 41 | 15.03 | 117 | Arachidonic acid | 0.53 | 1.424 | 0.3116 |
| 42 | 13.62 | 217 | myo-Inositol | 0.619 | 0.807 | 0.1552 |
| 43 | 7.25 | 117 | Glycerol | 0.592 | 0.911 | 0.2024 |
| 44 | 12.26 | 103 | Fructose | 0.588 | 0.918 | 0.3479 |
| 45 | 12.38 | 205 | Glucose | 0.52 | 0.999 | 0.9894 |
| 46 | 12.52 | 205 | Glucose | 0.52 | 1.022 | 0.6353 |
| 47 | 12 | 191 | 1.5-Anhydroglucitol | 0.531 | 1.028 | 0.9199 |
| 48 | 17.24 | 361 | Maltose | 0.612 | 1.188 | 0.3224 |
| 49 | 16.69 | 361 | Sucrose | 0.546 | 18.71 | 0.2991 |

TABLE 3-1

| No. | RT (min) | Unique Mass | Metabolites | AUC | Fold Change (DME/DB) | t-test |
|---|---|---|---|---|---|---|
| 50 | 7.11 | 320.5 | 20-HETE | 0.598 | 0.301 | 0.2217 |
| 51 | 3.96 | 352.5 | 15-keto Prostaglandin F2α | 0.75 | 0.341 | 0.0134 |
| 52 | 3.91 | 350.5 | 15-keto Prostaglandin E2 | 0.719 | 0.491 | 0.1439 |
| 53 | 3.35 | 370.5 | Thromboxane B2 | 0.598 | 0.643 | 0.4696 |
| 54 | 4.32 | 352.5 | 13,14-dihydro-15-keto Prostaglandin D2 | 0.617 | 0.746 | 0.5744 |
| 55 | 5.11 | 336.5 | 5(S)-HpETE | 0.624 | 0.752 | 0.2161 |
| 56 | 7 | 320.5 | (±)11-HETE | 0.624 | 0.775 | 0.3183 |
| 57 | 7.24 | 320.5 | (±)8(9)-EET | 0.588 | 0.783 | 0.4773 |
| 58 | 7.07 | 320.5 | (±)12-HETE | 0.579 | 0.804 | 0.352 |
| 59 | 7.29 | 320.5 | (±)5-HETE or (±)8-HETE | 0.586 | 0.805 | 0.4086 |
| 60 | 4.94 | 336.5 | (±)12-HpETE | 0.505 | 0.848 | 0.5845 |
| 61 | 3.74 | 625.8 | Leukotriene C4 | 0.505 | 0.853 | 0.6197 |
| 62 | 4.48 | 334.5 | Prostaglandin A2 | 0.526 | 0.878 | 0.8179 |
| 63 | 3.88 | 352.5 | Prostiglandin D2 | 0.586 | 0.915 | 0.7283 |
| 64 | 4.61 | 334.5 | Prostaglandin J2 | 0.524 | 0.991 | 0.9806 |
| 65 | 8.02 | 318.5 | 5-OxoETE | 0.548 | 1.041 | 0.9355 |
| 66 | 4.94 | 338.5 | (±)11(12)-DiHET or (±)14(15)-DiHET | 0.557 | 1.06 | 0.8009 |

TABLE 3-2

| No. | RT (min) | Unique Mass | Metabolites | AUC | Fold Change (DME/DB) | t-test |
|---|---|---|---|---|---|---|
| 67 | 7.14 | 320.5 | (±)5(6)-EET | 0.574 | 1.115 | 0.7319 |
| 68 | 3.64 | 332.5 | Leukotriene A4 methyl ester | 0.519 | 1.14 | 0.3959 |
| 69 | 4.08 | 496.7 | Leukotriene D4 | 0.605 | 1.203 | 0.5726 |
| 70 | 5.17 | 336.5 | Leukotriene B4 | 0.562 | 1.22 | 0.5217 |
| 71 | 6.81 | 320.5 | (±)15-HETE | 0.655 | 1.274 | 0.3533 |
| 72 | 7.24 | 318.5 | 15-OxoETE | 0.812 | 1.319 | 0.0015 |
| 73 | 7.28 | 320.5 | (±)9-HETE | 0.602 | 1.373 | 0.3123 |
| 74 | 4.5 | 334.5 | Prostaglandin B2 | 0.595 | 1.453 | 0.4526 |
| 75 | 3.99 | 352.5 | Prostaglandin E2 or Prostaglandin H2 | 0.648 | 1.463 | 0.3641 |
| 76 | 7.28 | 320.5 | (±)11(12)-EET or (±)14(15)-EET | 0.686 | 1.465 | 0.0815 |
| 77 | 4.01 | 352.5 | 20-hydroxy Leukotriene B4 | 0.602 | 1.479 | 0.4298 |
| 78 | 6.07 | 318.5 | 12-OxoETE | 0.867 | 1.526 | 0.0012 |
| 79 | 3.38 | 368.5 | 11-dehydro Thromboxane B2 | 0.538 | 1.578 | 0.448 |
| 80 | 4.5 | 354.5 | 13,14-dihydro-15-keto Prostaglandin F2α | 0.571 | 2.816 | 0.3957 |
| 81 | 3.98 | 352.5 | Lipoxin B4 | 0.586 | 4.364 | 0.1504 |
| 82 | 3.02 | 366.5 | 20-carboxy Leukotriene B4 | 0.743 | 5.575 | 0.0121 |

TABLE 3-3

| No. | RT (min) | Unique Mass | Metabolites | AUC | Fold Change (DME/DB) | t-test |
|---|---|---|---|---|---|---|
| 83 | 3.72 | 354.5 | Prostaglandin F2α | 0.543 | 6.221 | 0.2511 |
| 84 | 3.25 | 370.5 | 6-keto Prostaglandin F1α | 0.536 | 13657142858 | 0.3092 |
| 85 | 4.88 | 336.5 | 15(S)-HpETE | 0.607 | 22557142858 | 0.0661 |
| 86 | 7.65 | 344.5 | (±)4-HDHA | 0.69 | 0.757 | 0.0752 |
| 87 | 7.16 | 344.5 | (±)20-HDHA | 0.669 | 0.769 | 0.1138 |
| 88 | 7.39 | 344.5 | (±)7-HDHA | 0.524 | 0.895 | 0.8666 |
| 89 | 7.38 | 344.5 | (±)8-HDHA | 0.65 | 0.908 | 0.6225 |
| 90 | 7.06 | 344.5 | (±)17-HDHA | 0.531 | 0.923 | 0.9411 |
| 91 | 7.06 | 344.5 | (±)16-HDHA | 0.595 | 0.939 | 0.7086 |
| 92 | 5.01 | 360.5 | 10(S),17(S)-DiHDHA | 0.558 | 0.966 | 0.6005 |
| 93 | 7.24 | 344.5 | (±)10-HDHA | 0.505 | 1.13 | 0.5592 |
| 94 | 7.22 | 344.5 | (±)13-HDHA | 0.538 | 1.187 | 0.3507 |
| 95 | 6.4 | 318.5 | (±)15-HEPE | 0.617 | 0.812 | 0.4395 |
| 96 | 6.6 | 318.5 | (±)11(12)-EpETE | 0.633 | 0.887 | 0.5893 |
| 97 | 6.54 | 318.5 | (±)12-HEPE | 0.55 | 0.891 | 0.6076 |

TABLE 3-4

| No. | RT (min) | Unique Mass | Metabolites | AUC | Fold Change (DME/DB) | t-test |
|-----|----------|-------------|-------------|-----|----------------------|--------|
| 98 | 3.88 | 350.5 | Prostaglandin D3 | 0.634 | 0.898 | 0.9934 |
| 99 | 6.52 | 318.5 | (±)18-HEPE | 0.567 | 0.924 | 0.7107 |
| 100 | 3.77 | 350.5 | Prostaglandin E3 | 0.518 | 1.417 | 0.3548 |
| 101 | 7.53 | 294.4 | 9-OxoODE | 0.755 | 0.692 | 0.0225 |
| 102 | 7.26 | 294.4 | 13-OxoODE | 0.617 | 0.48 | 0.1317 |
| 103 | 5.18 | 314.5 | (±)12(13)-DiHOME | 0.643 | 0.822 | 0.2681 |
| 104 | 6.88 | 296.5 | (±)9(10)-EpOME | 0.624 | 0.838 | 0.3235 |
| 105 | 5.3 | 314.5 | (±)9(10)-DiHOME | 0.586 | 0.914 | 0.7023 |
| 106 | 7.76 | 296.5 | (±)9-HODE or (±)13-HODE | 0.743 | 0.924 | 0.0195 |
| 107 | 6.15 | 294.4 | 9(S)-HOTrE | 0.61 | 0.931 | 0.7274 |
| 108 | 6.6 | 312.4 | 13(S)-HpODE | 0.548 | 1.037 | 0.8402 |
| 109 | 6.56 | 312.4 | 9(S)-HpODE | 0.567 | 1.067 | 0.8127 |

<Experimental Example 3> Confirmation of
Metabolic Difference According to DME

Figure 5:
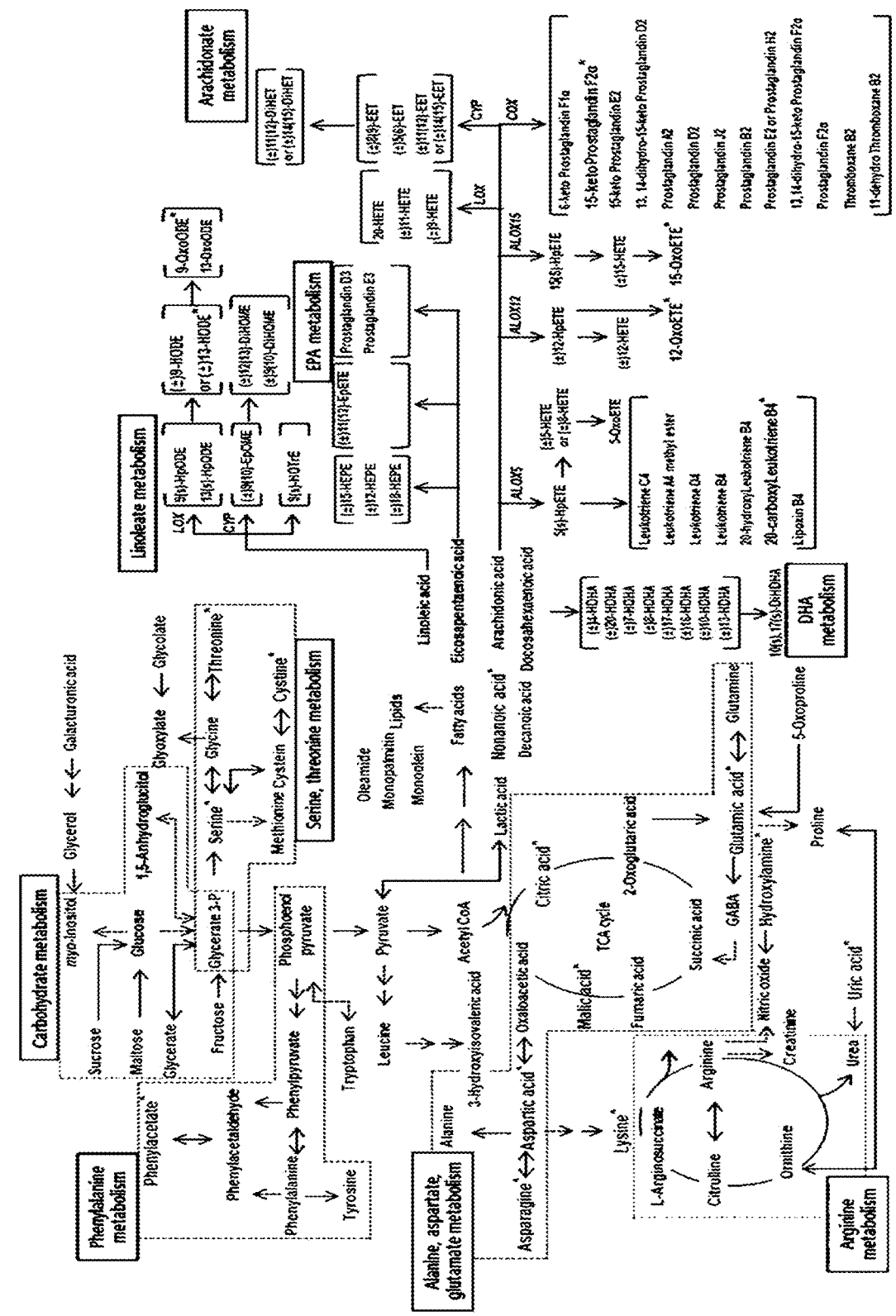
FIG. 5 is a diagram illustrating a metabolic pathway constructed to describe relations between DME and metabolisms.

In the analysis of plasma metabolites of subjects regardless of DME, various metabolites were selected as differential factors, and metabolic pathways were constructed to explain a relationship between metabolism and DME (FIG. 5). In the constructed pathways, carbohydrate, phenylalanine, alanine, aspartic acid, glutamic acid, arginine and oxylipins metabolisms (linoleate, eicosapentaenoate, arachidonate and docosahexaenoate metabolisms) had differences according to the presence or absence of DME. In particular, it was confirmed that metabolites such as serine, threonine, alanine, aspartate and glutamate and a TCA metabolic pathway were significantly reduced in non-DME subjects compared to non-DME subjects. For oxylipins metabolism, the relative metabolite levels of oxylipin precursor fatty acids such as linoleic acid, eicosapentaenoic acid, arachidonic acid and docosahexaenoic acid had no significant difference between DME and non-DME subjects. However, the relative amounts of oxylipins produced from other precursor fatty acids showed a significant difference, and among them, most of the oxylipins involved in linoleate, EPA and DHA metabolisms had relatively low metabolite levels in non-DME subjects compared to non-DME subjects. In particular, in the linoleate metabolism, oxylipins produced by lipoxygenase, peroxidase and dehydrogenases such as 9-HODE or 13-HODE and 9-oxo ODE were present at significantly lower levels in subjects with DME than in subjects without DME. For the arachidonate metabolism, various oxylipins had increased and decreased metabolism due to DME compared to non-DME subjects. Among them, it was confirmed that the levels of 20-carboxy leukotriene B4, 12-oxo ETE and 15-oxo ETE catalyzed by various enzymes including hydroxylase, carboxylase, lipoxygenase, peroxidase and dehydrogenase were significantly increased in DME. Meanwhile, 15-ketoprostaglandin F2a produced by the dehydrogenase activity showed a significantly reduced level in DME subjects.

Accordingly, in the present invention, amino acids, organic compounds and oxylipins as blood metabolites, that were statistically significantly differentiated from the control group, were selected from type 2 diabetes patients. Among them, as the blood metabolites, asparagine, aspartic acid, glutamic acid, cysteine, lysine, citric acid, and uric acid, and 12-oxo ETE, 15-oxo ETE, 9-oxo ODE, and 20-carboxy leukotriene B4, which were oxylipins, were confirmed to have cutoff values of AUC>0.7. In addition, the blood metabolites showed a significant difference between a DME patient group and a non-DME patient group, and thus were confirmed to be usable for accurate diagnosis of DME.

The invention claimed is:

1. A method for providing information required for diagnosis of diabetic macular edema comprising:
   measuring expression levels of (i) all of asparagine, aspartic acid, glutamic acid, cysteine, lysine, citric acid and uric acid, and (ii) at least one of 12-oxo ETE, 15-oxo ETE, 9-oxo ODE and 20-carboxy leukotriene B4 in a biological sample of a subject; and
   comparing the measured expression levels of (i) and (ii) above with corresponding expression levels of (i) and (ii) in a control sample.

2. The method for providing information of claim 1, wherein the method is to determine to have or be at a risk of diabetic macular edema when
   (i) the expression levels of all of asparagine, aspartic acid, glutamic acid, cysteine, lysine, citric acid, and uric acid are decreased, and
   (ii) the expression level of at least one of 12-oxo ETE, 15-oxo ETE, 9-oxo ODE, and 20-carboxy leukotriene B4 is increased,
   relative to the control sample.

3. The method for providing information of claim 1, wherein the cutoff values of (i) and (ii) above are AUC>0.7 or higher.

4. The method of claim 1, wherein the expression levels of (i) and (ii) are measured using liquid chromatography-triple quadrupole mass spectrometry (LC-triple-Q-MS).

5. The method of claim 1, wherein the expression levels of (i) and (ii) are measured using gas chromatography-time-of-flight mass spectrometry (GC-TOF-MS).

6. A method for diagnosis of diabetic macular edema comprising:
   measuring expression levels of (i) all of asparagine, aspartic acid, glutamic acid, cysteine, lysine, citric acid and uric acid, and (ii) at least one of 12-oxo ETE, 15-oxo ETE, 9-oxo ODE and 20-carboxy leukotriene B4 in a biological sample of a subject; and
   comparing the measured expression levels of (i) and (ii) above with corresponding expression levels of (i) and (ii) in a control sample.

7. The method for diagnosis of diabetic macular edema of claim 6, wherein the method is to determine to have or be at a risk of diabetic macular edema when
   (i) the expression levels of all of asparagine, aspartic acid, glutamic acid, cysteine, lysine, citric acid, and uric acid are decreased, and
   (ii) the expression level of at least one of 12-oxo ETE, 15-oxo ETE, 9-oxo ODE, and 20-carboxy leukotriene B4 is increased,
   relative to the control sample.

8. The method of claim 6, wherein the expression levels of (i) and (ii) are measured using liquid chromatography-triple quadrupole mass spectrometry (LC-triple-Q-MS).

9. The method of claim 6, wherein the expression levels of (i) and (ii) are measured using gas chromatography-time-of-flight mass spectrometry (GC-TOF-MS).

* * * * *